United States Patent [19]

Fogelman

[11] Patent Number: 5,105,851
[45] Date of Patent: Apr. 21, 1992

[54] APPARATUS FOR MULTI-PATH FLOW REGULATION

[75] Inventor: Kimber D. Fogelman, Newark, Del.

[73] Assignee: Hewlett-Packard Company, Palo Alto, Calif.

[21] Appl. No.: 599,330

[22] Filed: Oct. 17, 1990

[51] Int. Cl.$^5$ .............................................. F16K 11/06
[52] U.S. Cl. ........................... 137/625.11; 73/863.72; 137/625.46; 137/625.47
[58] Field of Search ............ 137/625.11, 625.46, 137/625.47; 73/863.72

[56] References Cited

U.S. PATENT DOCUMENTS

| | | | |
|---|---|---|---|
| 2,719,426 | 10/1955 | Lamb et al. | 137/625.11 X |
| 3,223,123 | 12/1965 | Young | 137/625.46 |
| 3,368,385 | 2/1968 | Harvey | 73/863.72 |
| 3,411,525 | 11/1968 | Auger | 137/625.46 X |
| 3,477,207 | 11/1969 | Auger | 137/625.46 X |
| 3,508,582 | 4/1970 | Aulisa | 137/625.11 |
| 3,933,436 | 1/1976 | Naono | 137/625.11 X |
| 4,506,558 | 3/1985 | Bakalyar | 73/863.72 |
| 4,625,569 | 12/1986 | Toei et al. | 73/863.72 |
| 4,690,179 | 9/1987 | Bleth et al. | 137/625.46 X |
| 4,706,627 | 11/1987 | Miwa et al. | 137/625.46 X |

Primary Examiner—Gerald A. Michalsky

[57] ABSTRACT

Valve assemblies are provided which comprise a housing having a common port and n peripheral ports, where n is an even integer greater than or equal to 4. The valve assemblies further comprise a valve plug contained within the housing. The valve plug comprises a distribution channel capable of fluid communication with the common port and at least one of the peripheral ports, and (n/2)−1 switching channels capable of fluid communication with at least two of the peripheral ports.

26 Claims, 15 Drawing Sheets

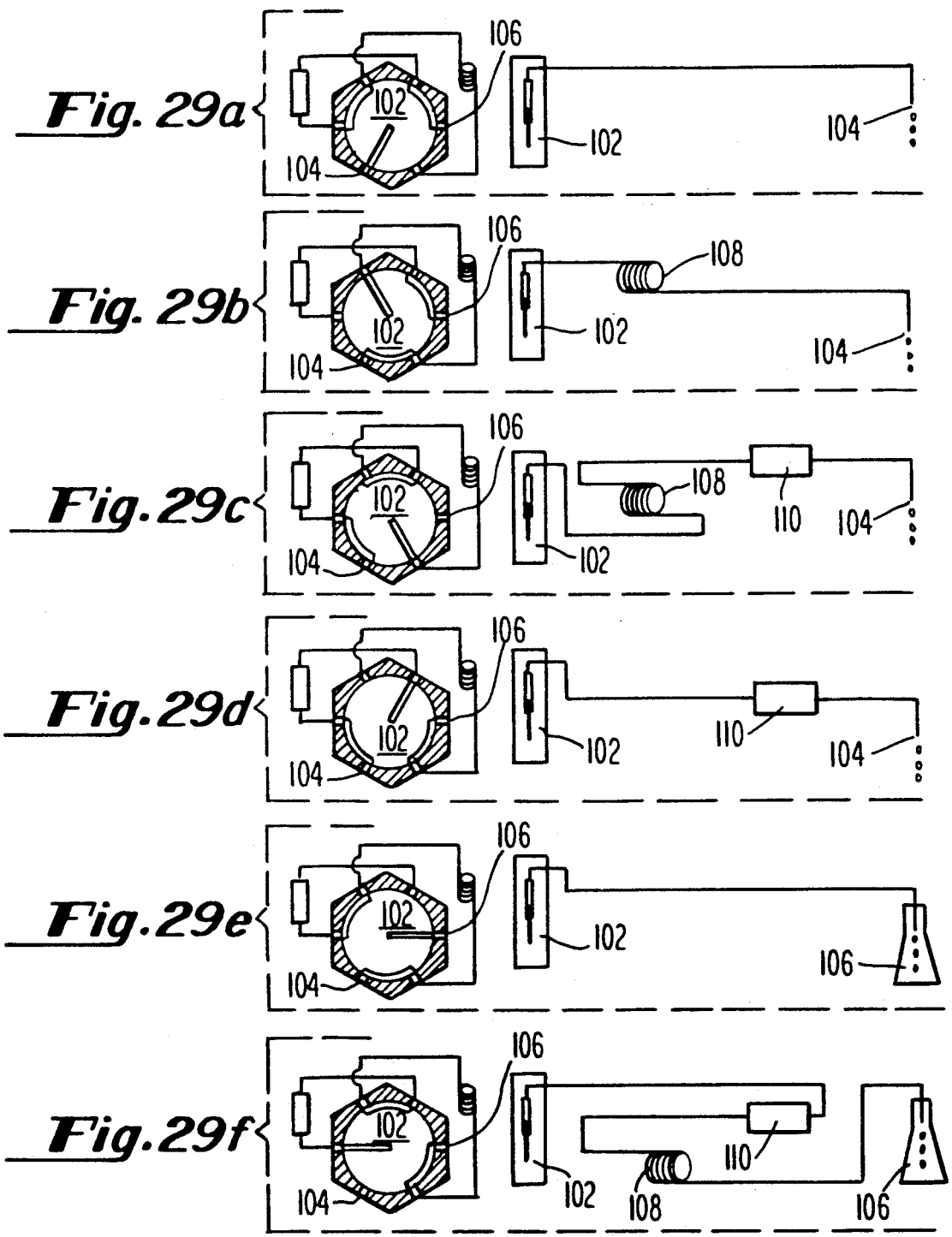

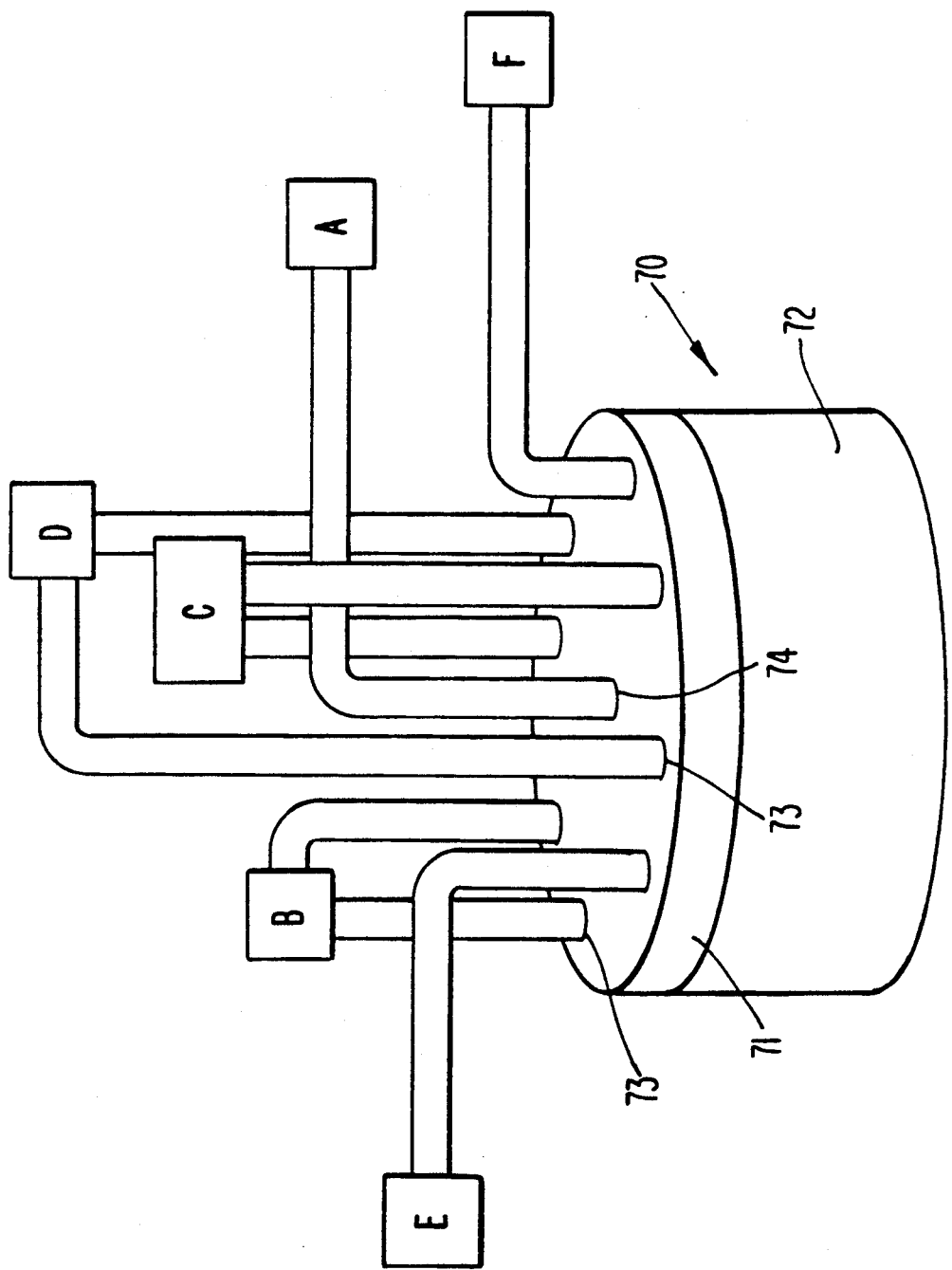

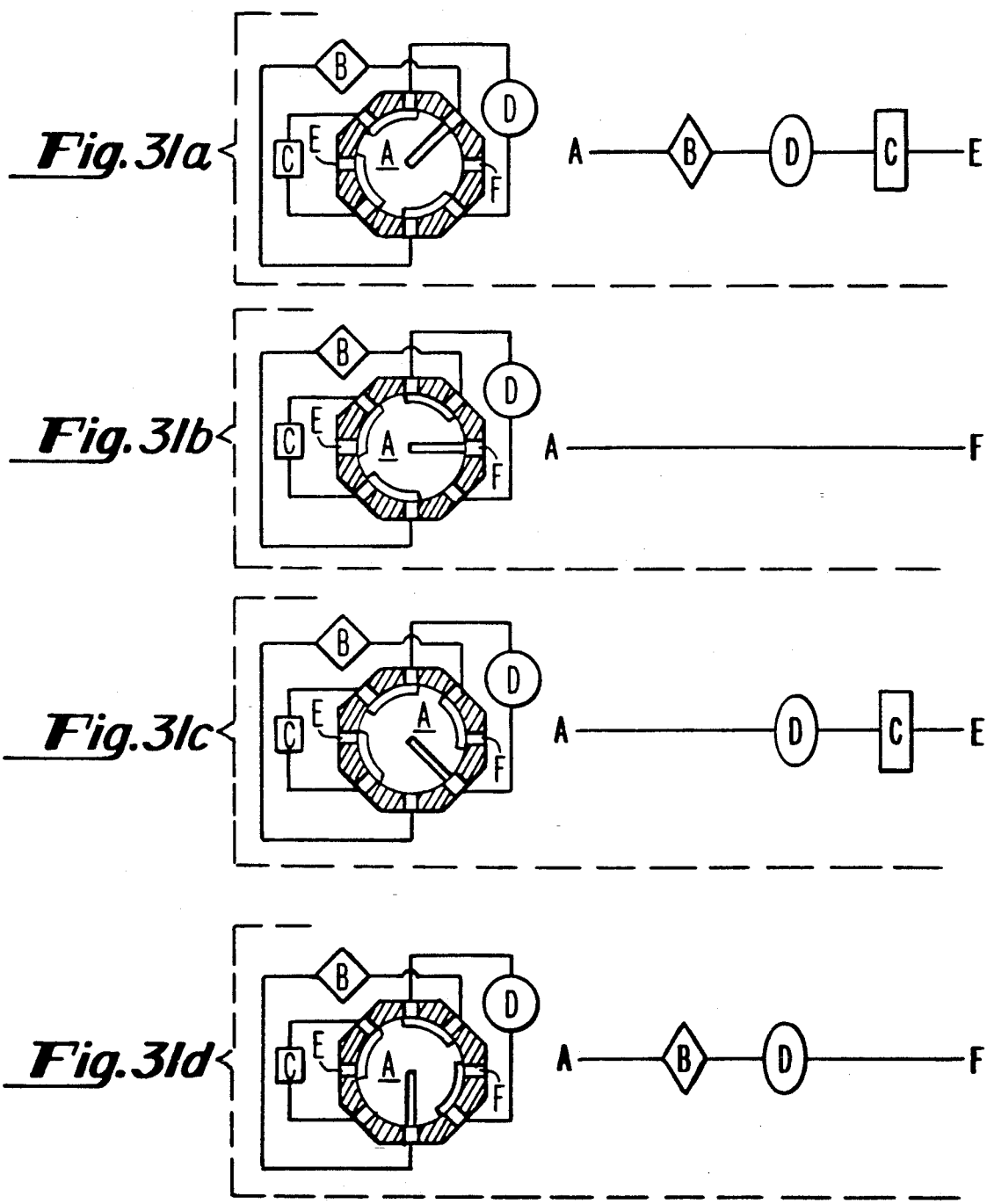

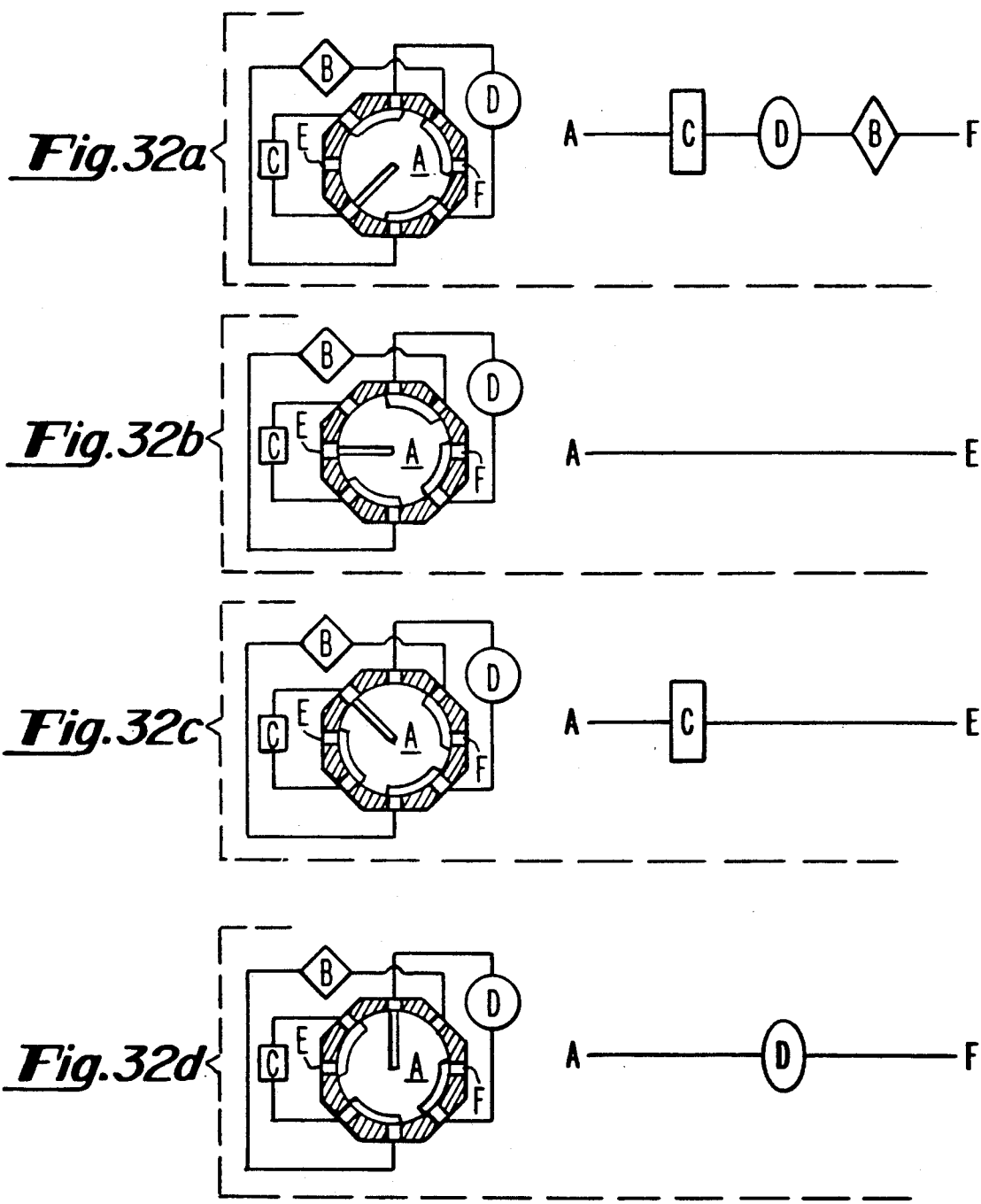

APPARATUS FOR MULTI-PATH FLOW REGULATION

BACKGROUND OF THE INVENTION

This invention relates to the regulation of fluid flow and, more particularly, to the switching of fluid flow between multiple discrete paths by means of a single valve assembly.

Instruments which rely upon regulated fluid flow are commonly employed in a wide variety of applications, such as sample purification, chemical analysis, clinical assay, and industrial processing. Such instruments typically function through either continuous or pulsed fluid flow. It will be appreciated that a pulsed-flow instrument is any device which operates by alternately maintaining and halting or reversing a flow stream through the device. This may be accomplished by combinations of valves and/or pumps to first initiate the flow and then stop or reverse it.

Very often, pulsed-flow devices require multiple flow paths to operate efficiently. Generally, efficient operation requires combining flow-through components, such as sorbent columns and connective tubing, with terminal components, such as needles, pumps, and drains. Examples of pulsed-flow devices include laboratory water purification systems, syringe-type reagent dispensers, manual and automated solid phase extraction (SPE) instruments, supercritical fluid extraction (SCF) instruments, stopped-flow spectrophotometers, automated protein or nucleic acid sequencers and solid phase protein or nucleic acid synthesizers.

Pulsed-flow instruments can be contrasted with continuous-flow devices which during their normal operation require a constant, unidirectional flow. Continuous-flow instruments also require different flow configurations to prime the system during set up or to perform different methods of analysis. Examples of continuous-flow systems include high pressure liquid chromatographs (HPLC), gas chromatographs (GC), clinical analyzers, and flow-injection analyzers.

For both pulsed- and continuous-flow systems, at least two different flow paths are frequently required to, for example, isolate a component from the flow system, attach a component into the flow system, or rearrange the order of the components in the flow system. For many systems, three or more unique flow paths are necessary for optimum operation.

It is known that combinations of commercially available valves can be arranged to provide an infinite number of flow paths among the flow-through components and terminal components employed in a flow system. There exists the practical problem, however, of connecting the large number of valves required for some flow path combinations, especially when minimum volumes within the flow system are desirable. Another problem involves properly orienting all of the valves so as to allow the desired flow path. It will be appreciated that as additional valves are added to the flow system, solutions to both of these problems both more expensive and complex.

Rotary valve assemblies having more than two flow paths are available in a large variety of configurations. For example, radial valve assemblies such as depicted in FIGS. 1-7 are available from the Hamilton Corporation (Reno, Nev.). The valve assemblies comprise a housing (10) which comprises an outer face (11) and a sleeve (12). A common port (14) extends axially through the outer face and a plurality of peripheral ports (13) extend radially through the sleeve. The valve assemblies further comprise a circular valve plug (20) contained within the housing, having a a body (22) which has an end face (21) and a lateral face (23). Distribution valve assemblies—such as shown in FIGS. 1 and 6—have a circular, pore-like distribution channel (24) contained substantially within the body. Switching valve assemblies—such as shown in FIGS. 2 and 7—have semi-circular or square grooved switching channels (26) on the lateral face.

Another class of radial valve assemblies, depicted in FIGS. 8-13, are available from the Valco Corporation (Houston, Tex.). The valve assemblies comprise a housing (50) which comprises an outer face (51) and a sleeve (52). A common port (54) and a plurality of peripheral ports (53) extend radially through the sleeve. The valve assemblies further comprise a conical valve plug (60) contained within the housing, having a body (62) which has an end face (61) and a lateral face (63). Distribution valve assemblies—such as shown in FIGS. 8, 11, and 12—have a semi-circular or square grooved distribution channel (64) on the lateral face having an axial component ($64a$) and a radial component ($64b$). Switching valve assemblies—such as shown in FIGS. 9 and 13—have semi-circular or square grooved switching channels (66) on the lateral face.

An axial valve assembly such as depicted in FIGS. 14-18 is available from the Rheodyne Corporation (Cotati, Calif.). The valve assembly comprises a housing (70) which comprises a sleeve (72) and an outer face (71) in the form of a plate. The outer face comprises a common port (74) and a plurality of peripheral ports (73) extending axially through the entire thickness of the outer face. The valve assembly further comprises a circular valve plug (80) contained within the housing, comprising a body (88) having an end face (86). Distribution valve assemblies comprise semi-circular distribution channels (82) on the end face, while switching valve assemblies comprise switching channels (84) on the end face.

Most commercially-available rotary valves are either distribution type valves or switching (loop) type valves. Distribution valves are characterized by having a single distribution channel which can be turned or otherwise manipulated to connect the common port and any one of the peripheral ports in a point-to-point configuration. Thus, a distribution channel is capable of fluid communication with both the common port and one of the peripheral ports. The number of unique plug orientations for a distribution valve is determined by the number of peripheral ports the valve assembly comprises in addition to the common port. Peripheral ports not connected to the common port are usually excluded from the flow system. Hence, for each unique orientation of the valve plug only a single unique flow path is allowed.

Switching valves are characterized by providing internal connections between multiple, different sets of valve ports. Switching valves have switching channels which can be manipulated to connect two or more peripheral ports. Thus, a switching channel is capable of fluid communication with two or more peripheral ports. Typically, at least one terminal or flow-through component is connected to a switching valve at two peripheral ports. Fluid should flow from one peripheral port of the switching valve to the component and then from the component to the other peripheral port. As a result, components connected to switching valves have markedly different flow path depending on the valve orientation. Generally, switching valves contain half the number of internal channels as they have valve ports. The channels are symmetrically arranged so that only two unique positions of the plug are established. However, for each unique orientation of the valve plug, multiple flow paths through the valve may be allowed.

Combinations of distribution and switching valves are frequently used in pulsed- and continuous-flow systems to create a large variety of flow paths. However, multiple valve implementations involve a large number of external connections which increases the complexity, expense, and physical volume of the flow system. The complexity of such systems also introduces reliability concerns. Also, since these flow systems are typically automated, greater reliability and lower complexity are critical for successful instrument development.

Few examples are available in which a single valve exhibits properties of both a switching valve and a distribution valve. One example is the stream selection valve depicted in FIG. 19, which is available from the Valco Corporation. The purpose of this valve is to divert a single stream to a common outlet while maintaining flow in all the other streams. However, this valve requires 2n+1 ports to achieve a number, n, unique flow paths. It would be of great advantage to provide a valve assembly having fewer ports yet capable of providing more flow paths.

SUMMARY OF THE INVENTION

The present invention provides novel valve assemblies which comprise a housing having a common port and n peripheral ports, where n is an even integer greater than or equal to 4. The valve assemblies further comprise a valve plug contained within the housing. The valve plug comprises a distribution channel capable of fluid communication with the common port and at least one of the peripheral ports, and $(n/2)-1$ switching channels capable of fluid communication with at least two of the peripheral ports.

The orientation of the channels on the plug is such that when the distribution channel of the plug is aligned with one of the peripheral ports of the housing, the switching channels each internally connect a unique pair of peripheral ports. Further, only $n-1$ peripheral ports are in communication with the distribution or switching channels at one time; the remaining port is blocked from the internal flow channels in the valve.

The present invention also provides systems for the regulation of fluid flow. The systems comprise at least one terminal component, a valve assembly according to this invention in fluid communication with the terminal component, and at least one flow-through component in fluid communication with the valve assembly. Different orientations of the valve plug within the housing allow for the isolation of terminal and/or flow-through components from the flow system, the attachment of terminal and/or flow-through components into the flow system, and the rearrangement of the flow-through components in the flow system.

BRIEF DESCRIPTION OF THE DRAWINGS

FIGS. 29a-29f show possible plug orientations for a flow system corresponding to the system depicted in FIG. 28, comprising a radial 6-port valve assembly in place of the axial 6-port valve assembly.

FIG. 30 depicts a flow system according to the present invention, comprising an axial 8-port valve assembly.

FIGS. 31a–31d and 32a–32d show possible plug orientations for a flow system corresponding to the system depicted in FIG. 30, comprising a radial 8-port valve assembly in place of the axial 8-port valve assembly.

DETAILED DESCRIPTION OF THE INVENTION

Figure 1:
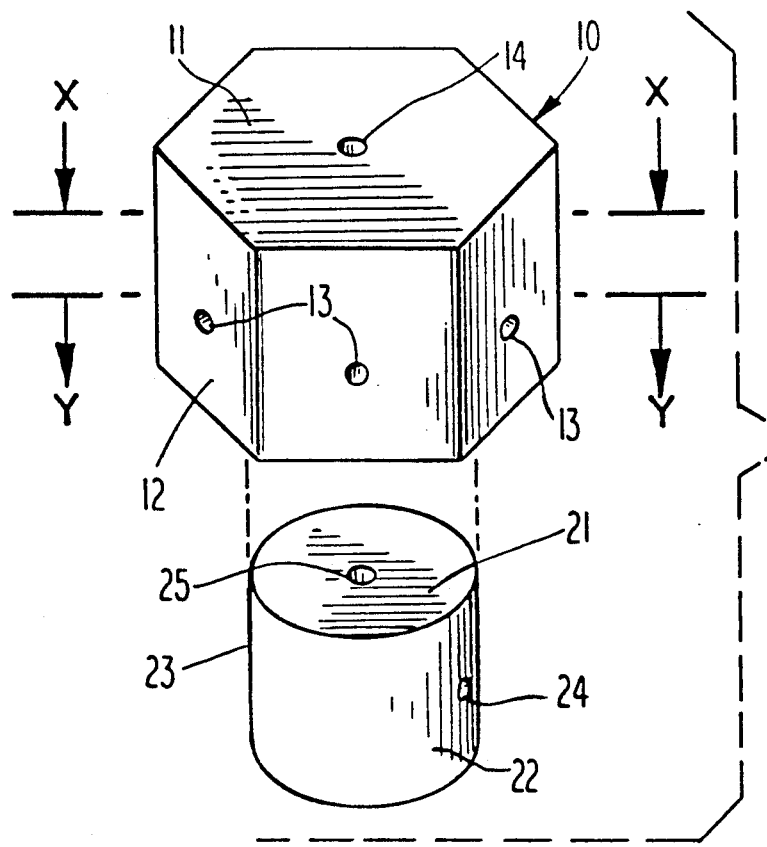
FIG. 1 is an exploded perspective view of a radial 6-port distribution valve assembly according to the prior art.
Figure 2:
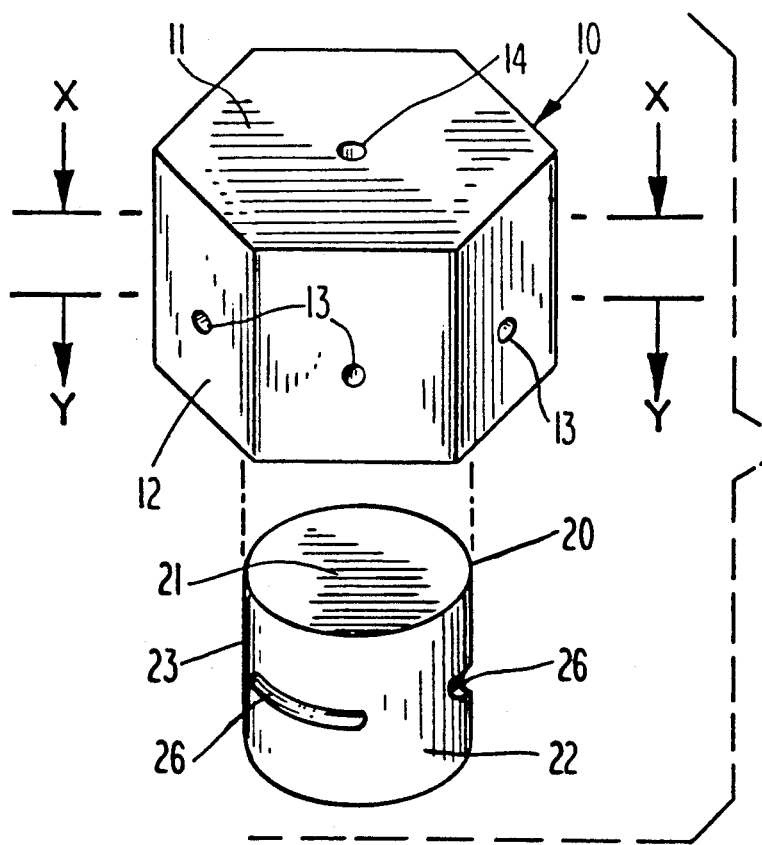
FIG. 2 is an exploded perspective view of a radial 6-port switching valve assembly according to the prior art.
Figure 3:
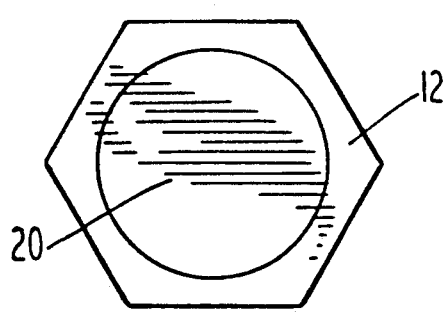
FIG. 3 is a bottom view of the radial valve assemblies of FIG. 1 and FIG. 2.
Figure 4:
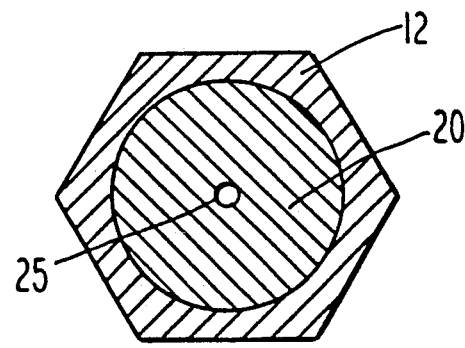
FIG. 4 is a cross-sectional view of the radial distribution valve assembly of FIG. 1, taken at line X—X.
Figure 5:
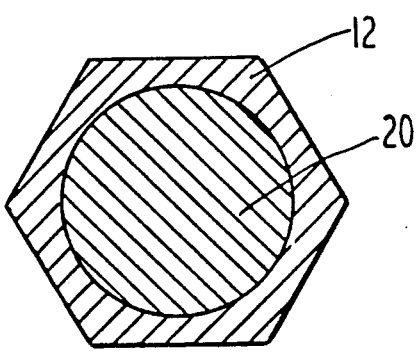
FIG. 5 is a cross-sectional view of the radial switching valve assembly of FIG. 2, taken at line X—X.
Figure 6:
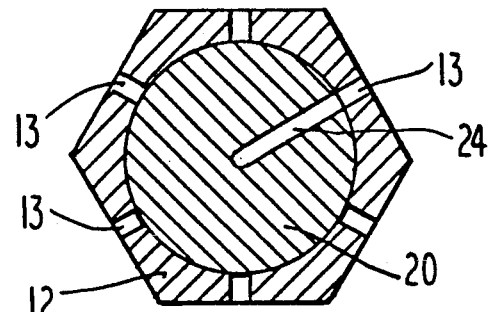
FIG. 6 is cross-sectional view of the radial distribution valve assembly of FIG. 1, taken at line Y—Y.
Figure 7:
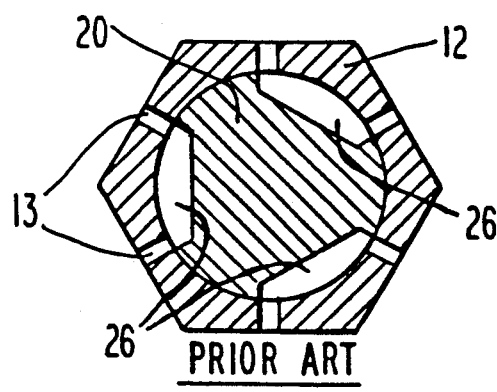
FIG. 7 is cross-sectional view of the radial switching valve assembly of FIG. 2, taken at line Y—Y.
Figure 8:
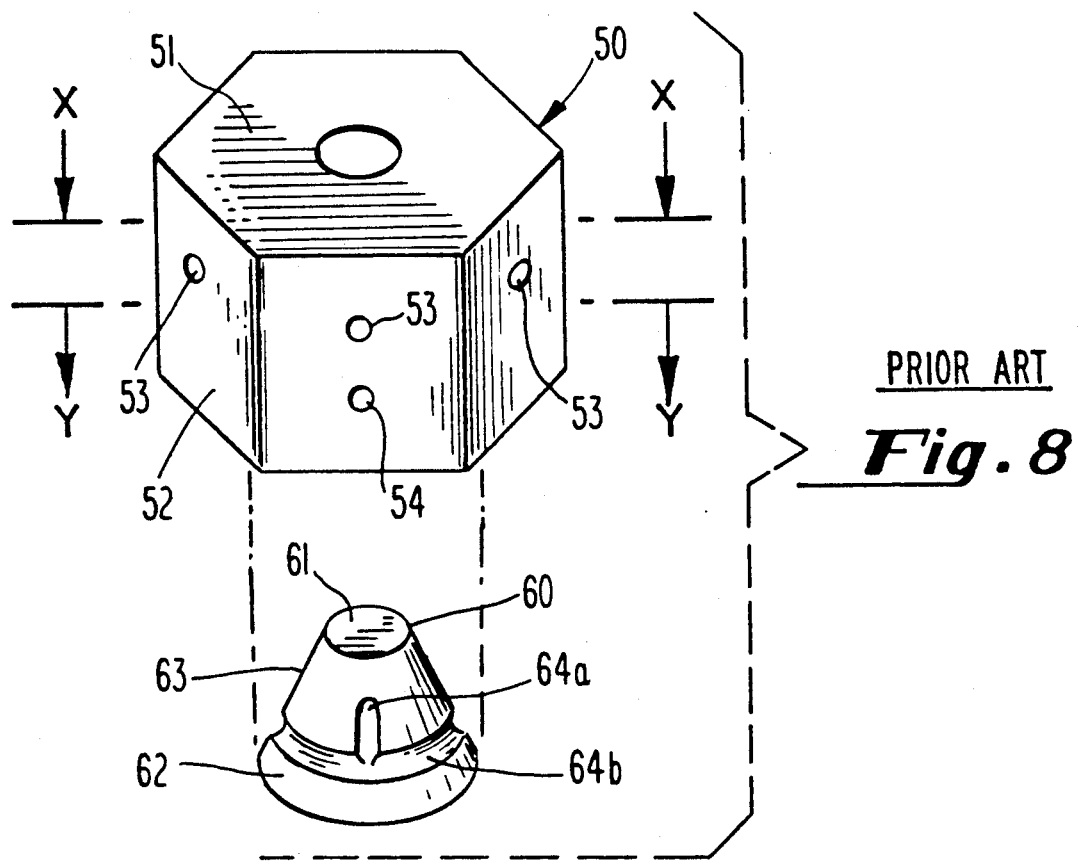
FIG. 8 is an exploded perspective view of a radial 6-port distribution valve assembly according to the prior art.
Figure 9:
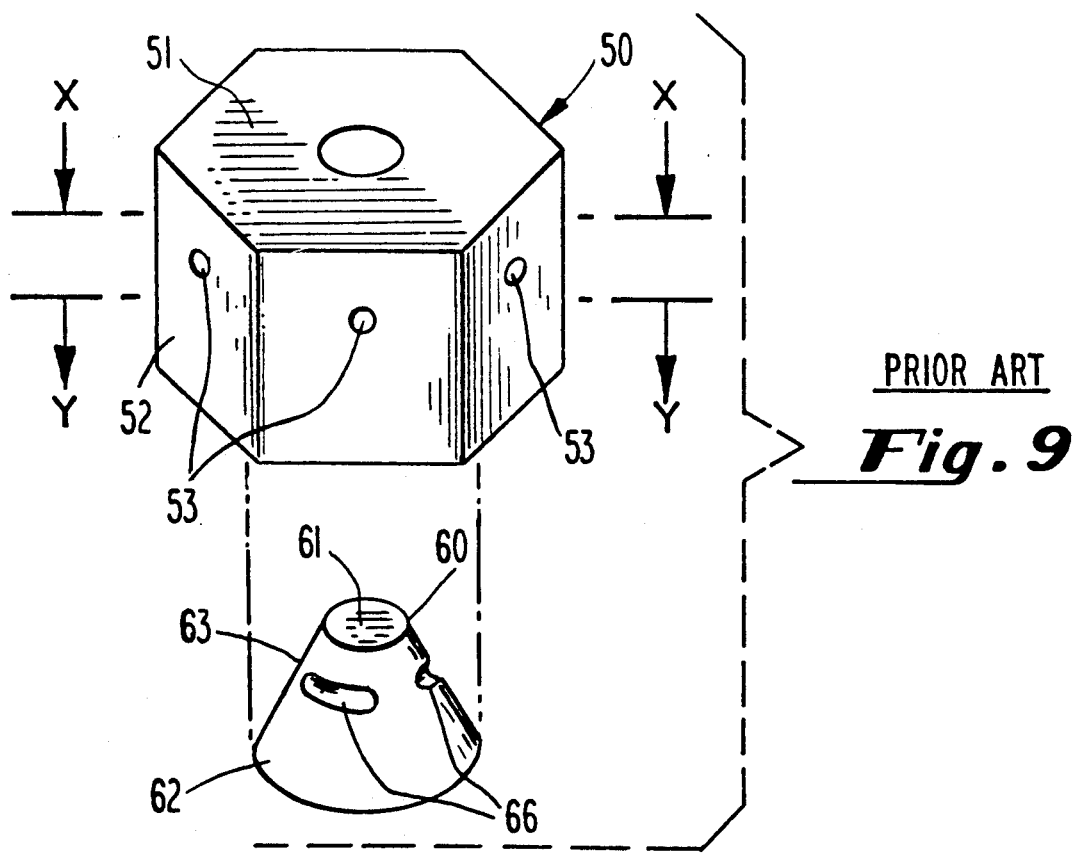
FIG. 9 is an exploded perspective View of a radial 6-port switching valve assembly according to the prior art.
Figure 10:
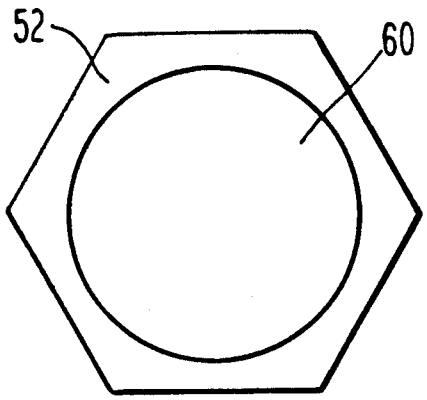
FIG. 10 is a bottom view of the radial valve assemblies of FIG. 8 and FIG. 9.
Figure 11:
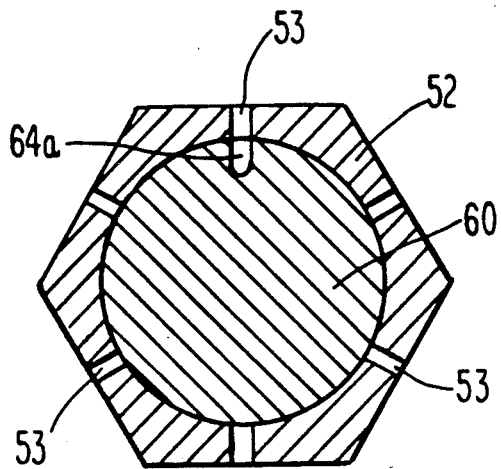
FIG. 11 is a cross sectional view of the radial distribution valve assembly of FIG. 8, taken at line X—X.
Figure 12:
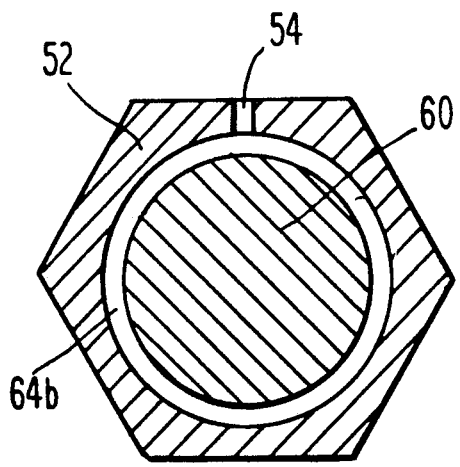
FIG. 12 is a cross-sectional view of the radial distribution valve assembly of FIG. 8, taken at line Y—Y.
Figure 13:
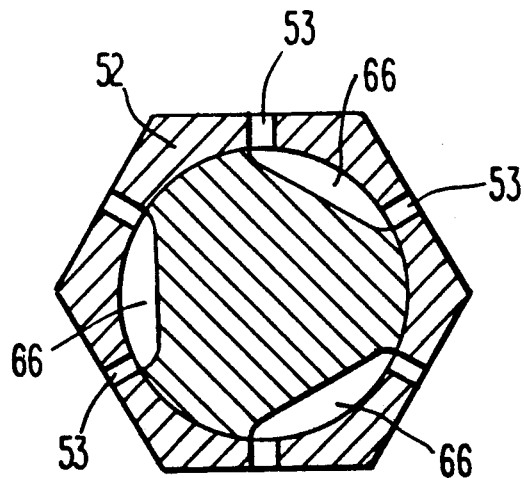
FIG. 13 is a cross-sectional view of the radial switching valve assembly of FIG. 9, taken at line X—X.
Figure 14:
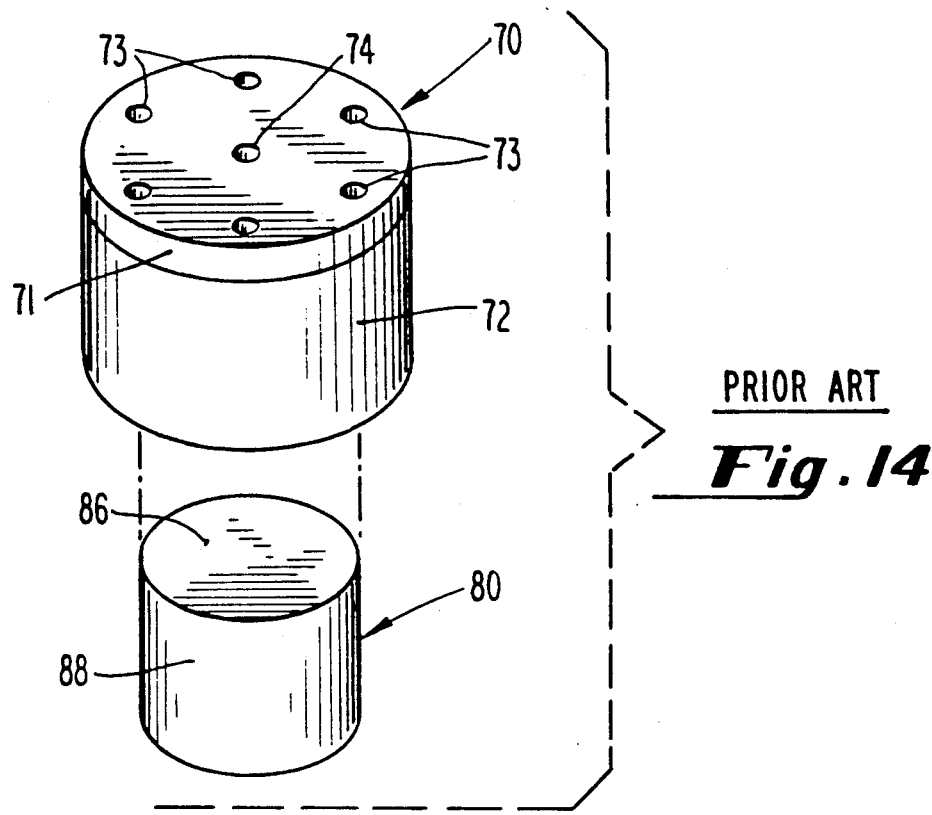
FIG. 14 is an exploded perspective view of an axial 6-port valve assembly according to the prior art.
Figure 15:
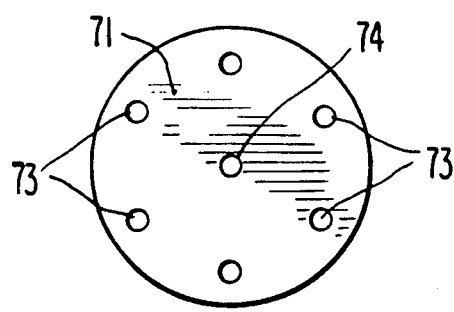
FIG. 15 is a top view of the axial valve assembly of FIG. 14.
Figure 16:
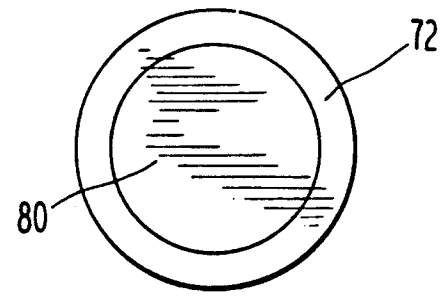
FIG. 16 is a bottom view of the axial valve assembly of FIG. 14.
Figure 17:
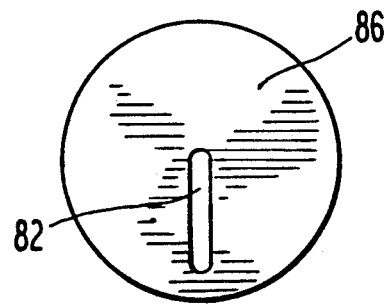
FIG. 17 is a top view of the plug end face of an axial 6-port distribution valve assembly according to the prior art.
Figure 18:
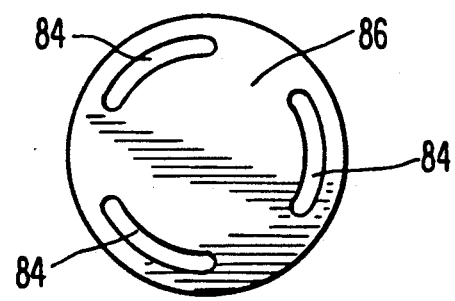
FIG. 18 is a top view of the plug end face of an axial 6-port switching valve assembly according to the prior art.
Figure 19:
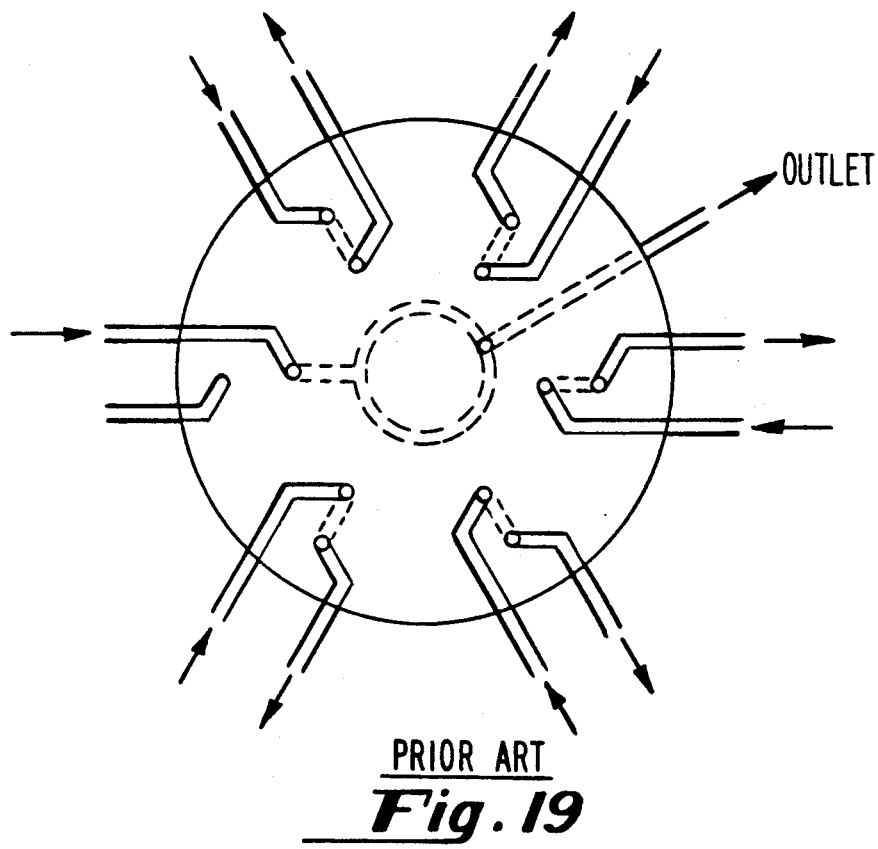
FIG. 19 is a diagrammatical representation of a radial stream selection valve assembly according to the prior art.
Figure 20:
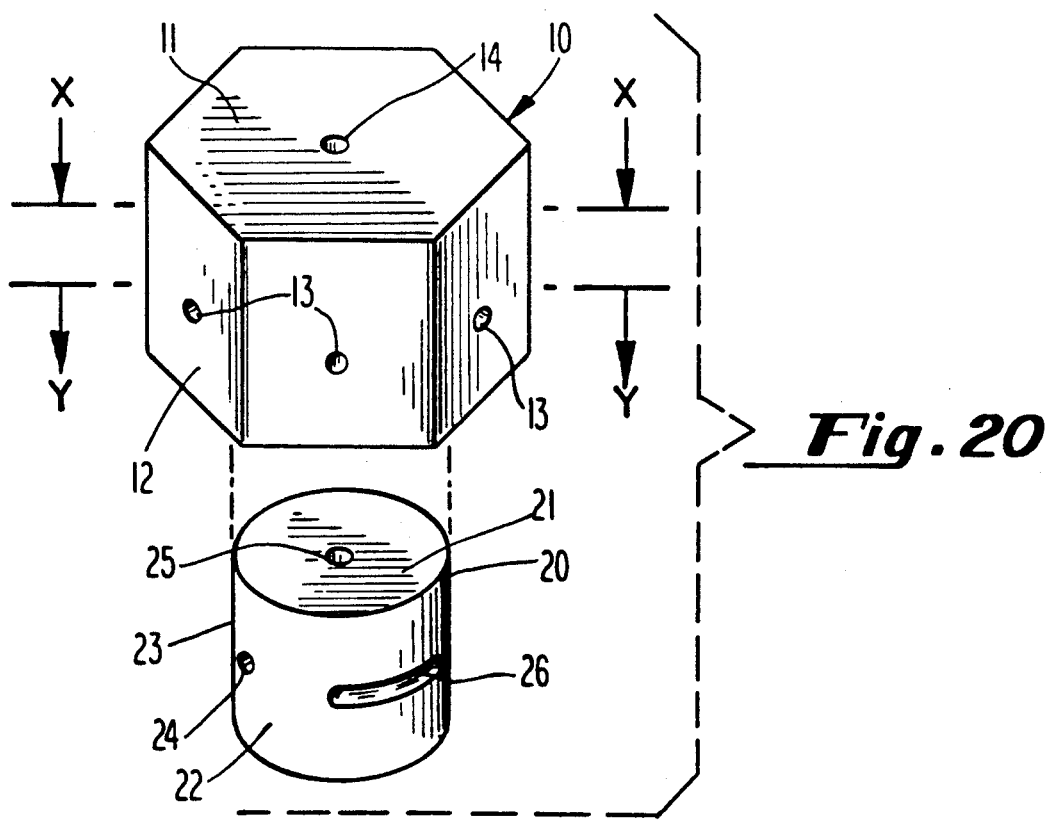
FIG. 20 is a radial, 6-port valve assembly according to the present invention.
Figure 21:
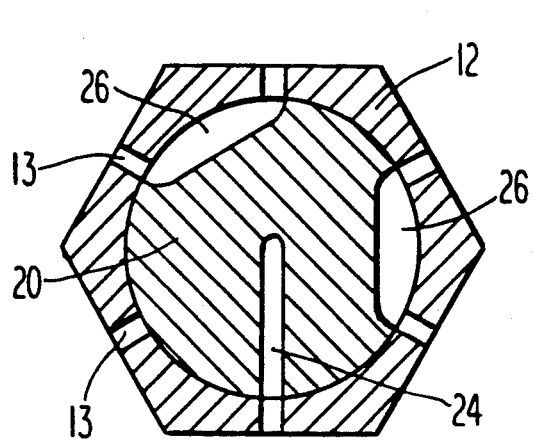
FIG. 21 is a cross-sectional view of the radial valve assembly of FIG. 20, taken at line Y—Y.
Figure 23:
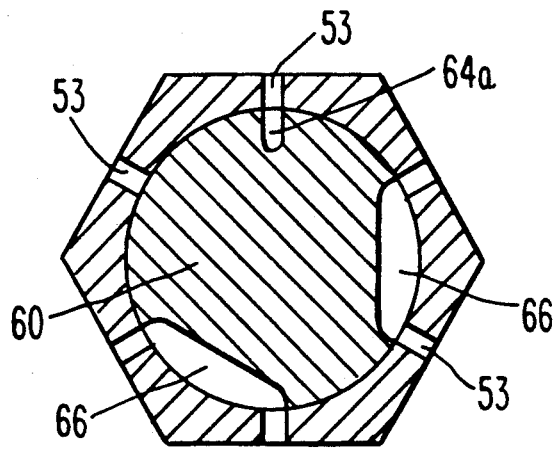
FIG. 23 is a cross-sectional view of the radial valve assembly of FIG. 22, taken at line X—X.
Figure 22:
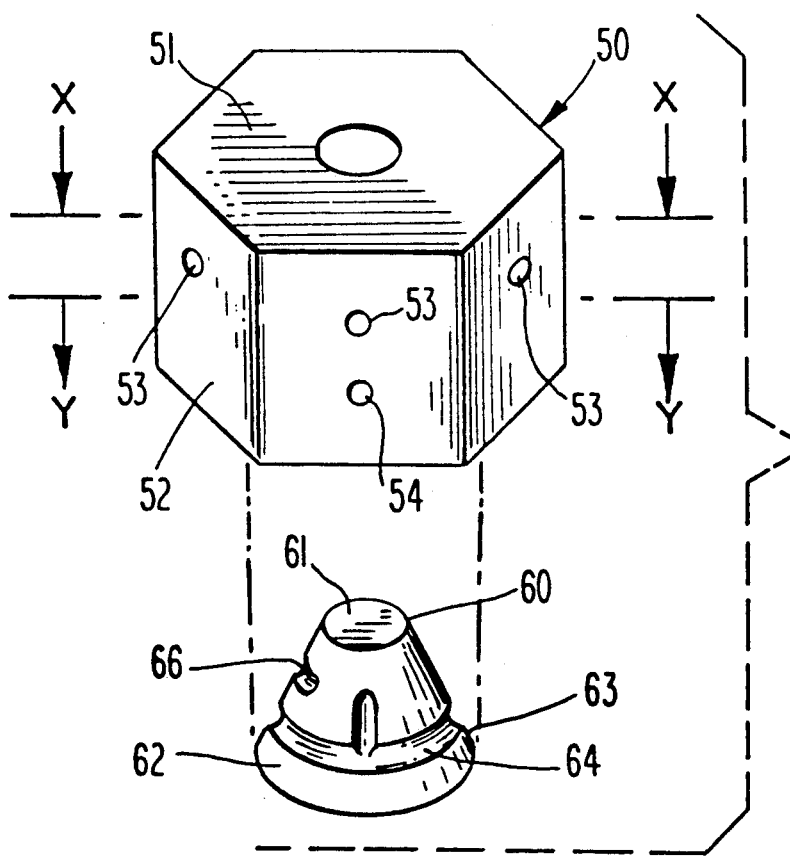
FIG. 22 is a radial, 6-port valve assembly according to the present invention.
Figure 24:
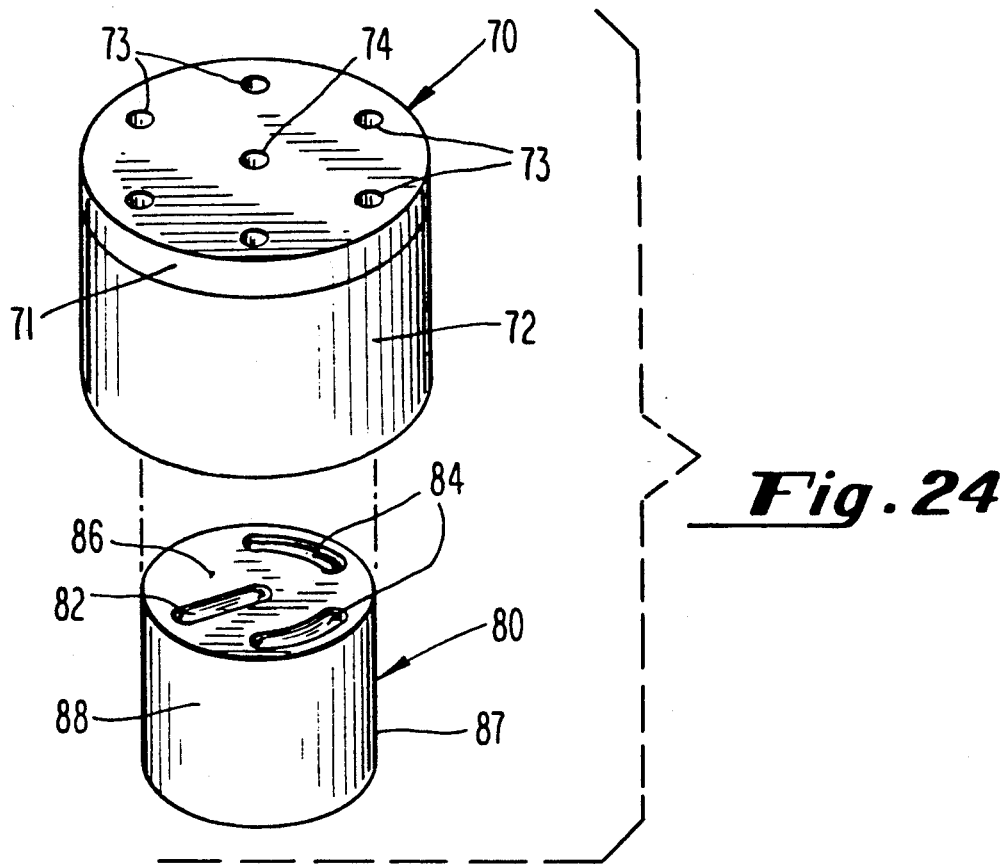
FIG. 24 is an axial, 6-port valve assembly according to the present invention.
Figure 25:
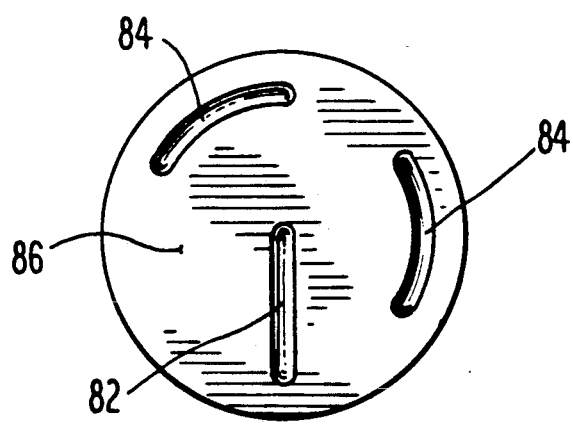
FIG. 25 is a top view of the plug end face of the axial valve assembly of FIG. 24.
Figure 26:
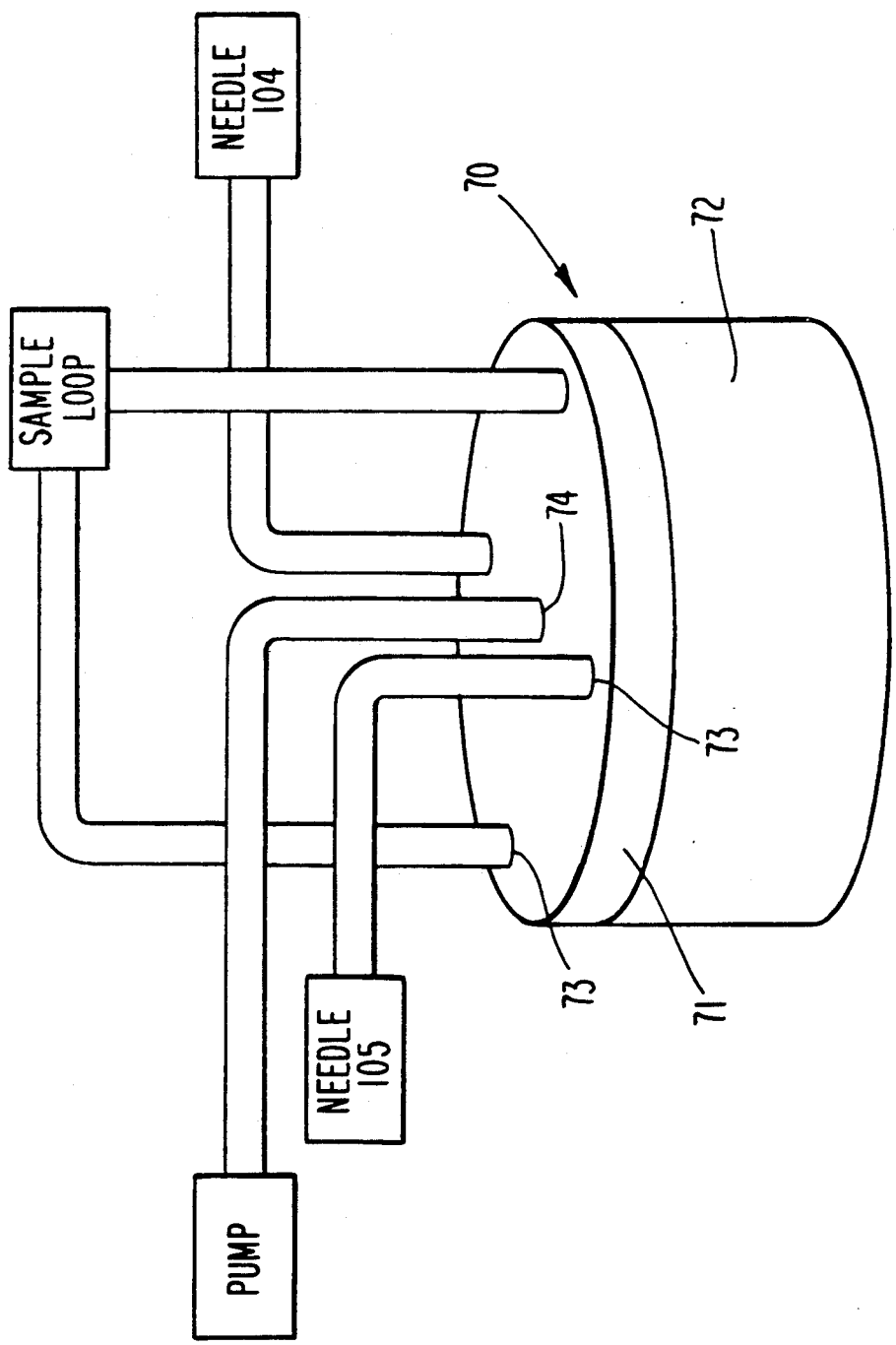
FIG. 26 depicts a flow system according to the present invention, comprising an axial 4-port valve assembly.

Preferred valve assemblies according to the present invention are depicted in FIGS. 20, 22, and 24. The valve assemblies of FIGS. 20 and 24 are particularly preferred. The valve assemblies comprise a housing (10, 50, or 70), which preferably comprises a sleeve (12, 52, or 72) attached to an outer face (11, 51, or 71). Housings can be fabricated from a wide variety of materials. It is preferred that housings comprise stainless steel and/or an organic polymer which is inert to the fluids regulated by the valve. Exemplary inert polymers are aramid polymers, acetal resins, and poly(tetrafluoroethylene)—such as available from the DuPont Company (Wilmington, Del.) under the tradenames Kevlar, Delrin, and Teflon, respectively—and poly(chlorotrifluoroethylene), such as available from the 3M Company (Newark, N.J.) under the tradename Kel-F. Poly(tetrafluoroethylene) and poly(chlorotrifluoroethylene) are preferred inert polymers.

The housing preferably comprises a common port (14, 54, or 74) and peripheral ports (13, 53, or 73). It will be appreciated that a common port is a port capable of fluid communication with each other port of the valve assembly, depending upon the orientation of the valve plug. Common ports preferably occupy a central location on the housing and, in turn, on the valve assembly. Peripheral ports are those ports other than the common port. Preferably, the peripheral ports are equally-spaced about the common port at the periphery of the housing. The common and peripheral ports are thus contained in the sleeve and/or the outer face.

The housings of this invention comprise n peripheral ports, where n is an even integer greater than or equal to 4. Preferably n is 4, 6, 8, 10, or 12. More preferably, n is 4, 6, or 8. Even more preferred are housings wherein n is 6. Valve assemblies wherein the housing comprises 6 peripheral ports are known as 6-port valves or 6-port valve assemblies.

Contained within the housing and in close physical contact therewith is a circular valve plug (20, 60, or 80) having a body (22, 62, or 88) which has an end face (21, 61, or 86) and a lateral face (23, 63, or 87). Valve plugs can be fabricated from a wide variety of materials. Preferred valve plugs comprise an organic polymer which is inert to the fluids regulated by the valve, as set forth above.

As exemplified by FIGS. 20–25, the valve plugs of this invention comprise a distribution channel (24, 64, or 82) and (n/2)−1 switching channels (26, 66, or 84). It will be appreciated by those skilled in the art that suitable channels for regulating fluid flow can have a wide variety of shapes and configurations. It is preferred that channels be configured such that there exists no axial plane of symmetry passing through the end face of the valve plug. It will be appreciated that such an asymmetric channel configuration avoids flow path duplication. Preferred valve plugs comprise circular, pore-like channels within the body of the valve plug, semi-circular or square grooved channels on the end face or lateral face of the valve plug, or combinations thereof. The channels can be created by any of the mechanical and/or chemical methods known in the art, such as etching, drilling, molding, or stamping.

The valve assemblies of the present invention are preferably one component in systems for the regulation of fluid flow. The flow systems preferably comprise a terminal component in fluid communication with the valve assembly. It will be appreciated that a terminal component is any apparatus or device connected by tubing, piping, or other suitable means to the valve assembly by a single peripheral port of the valve assembly. Thus, fluid pumps, needles, canulas, detectors, tubing, sorbent columns, solid phase support resins, filters, sample loops, and waste drains provide examples of terminal components.

Preferred flow systems further comprise a flow-through component. Flow-through components include any apparatus or device connected by tubing, piping, or other suitable means to the valve assembly by more than one peripheral port of the valve assembly. Tubing, sorbent columns, solid phase support resins, filters, sample loops, detectors, sample injection valves, and valving flow systems provide examples of flow-through components. Valve assemblies according to the present invention preferably meet the following criteria. They should be in a flow-allowed position when the distribution channel of the valve plug is aligned with any of the peripheral ports. They should contain exactly three port connections to terminal components of the flow system. They are preferably connected with at least one terminal component in a manner which allows flow either into or out of a channel aligned with the terminal component. Preferably, a terminal component is connected to the common port of the distribution channel of the valve. The valve assembly should also contain n−2 port connections to flow-through components of a flow system. Each flow-through component should be connected at two ports of the valve to provide a flow path between these two ports. The number of flow-through components is therefore (n/2)−1. Additionally, the two ports connected to a flow-through component preferably are not adjacent one another.

A flow system containing a valve assembly which meets these criteria will have at least one configuration of components having all of the following beneficial characteristics. Thus, the configuration will allow n unique flow paths which each join exactly two of the terminal components. A flow path is considered to be the path which includes the ports, channels and flow-through components which are in fluid communication with the two terminal components when the valve assembly is positioned in a flow-allowed orientation.

In such a flow system, only one flow path will be allowed for each unique flow-allowed orientation. The path connecting the third terminal component and any flow-through components will be terminated at the blocked port of the valve. The component connected to the common distribution port will be included as a terminal component in each possible flow path.

Also, the number of flow-through components included in a given flow path will range from zero to the maximum number of flow-through components. Exactly two flow paths will directly connect terminal components with no intervening flow-through components.

Additionally, two flow paths will include all flow-through components. The order of the flow-through components in the two flow paths will be reversed with respect to the terminal component connected to the common port. Further, the terminal component connected to a peripheral port will be different in each of these flow paths.

FIGS. 29a–29f illustrate a valve configuration for a 6-port valve with three terminal components—the pump (102), needle (104 or 105) and waste (106) positions—and two flow-through components—a sample loop (108) and sorbent column (110). This valve configuration is an example which exhibits the characteristics stated above. FIGS. 27a–27d and FIGS. 31a–31d and 32a–32d display 4-port and 8-port valves respectively configured according to the above rules. The set of unique flow paths for each configuration are displayed to the right of each flow-allowed orientation of the valve.

The advantages of the valve flow systems of the present invention include the reduction of external connections between valves by use of a single valve for flow path selection. External connections undesirably increase the volume of the flow system. Another advantage is that flow paths not connected to the distribution channel are dead-ended to prevent uncontrolled flow.

A further advantage of the present invention is that multiple valves need not be coordinated and monitored as with prior art systems. This results from all paths being switched simultaneously by a single turn of the valve plug. Also, considerable cost savings and lowered reliability concerns are recognized by reduction of the number of valves and actuators necessary to achieve multiple flow paths. Fewer valves also reduces the complexity of a flow system, which is desirable for automation of the stream selection procedure.

Additional objects, advantages, and novel features of the present invention will become apparent to those skilled in the art upon examination of the following examples thereof, which are not intended to be limiting.

EXAMPLE 1

A syringe pump is a common analytical instrument which is capable of aspirating and dispensing fluids. Syringe pumps are therefore useful for diluting samples, adding measured amounts of chemical reagents, transferring bulk quantities of reagent to small containers, or transferring fluids between two small containers.

Accurate dispensing of small volumes of reagent requires that the transfer line between the pump syringe and the needle, canula, tubing end or other type of dispensing tip be filled with an incompressible fluid. Generally, this fluid is also the reagent to be dispensed. For expensive reagents, it is desirable to minimize the volume of the transfer line, since any reagent remaining in this tubing is often flushed to a waste receptacle when a new reagent is required.

However, aspiration is commonly performed by providing a transfer line between the pump and needle. The transfer line preferably has sufficient volume to contain the aspirate, thus avoiding contamination of the syringe in the pump. During aspiration, the needle typically is lowered into the solution to be sampled and the syringe pump is drawn back to draw the solution into the sample loop. The aspirate may then be transferred to a second container by replacing the original solution container with a different container beneath the needle. A more desirable process would transfer the sample from the loop to a container positioned beneath a second needle. The advantage of such a process is that fewer container movements would be necessary to effect the transfer. Thus, a conflict occurs between the need for a minimum-volume transfer line for dispensing and the need for large volume transfer line for aspirating.

Figure 27A:
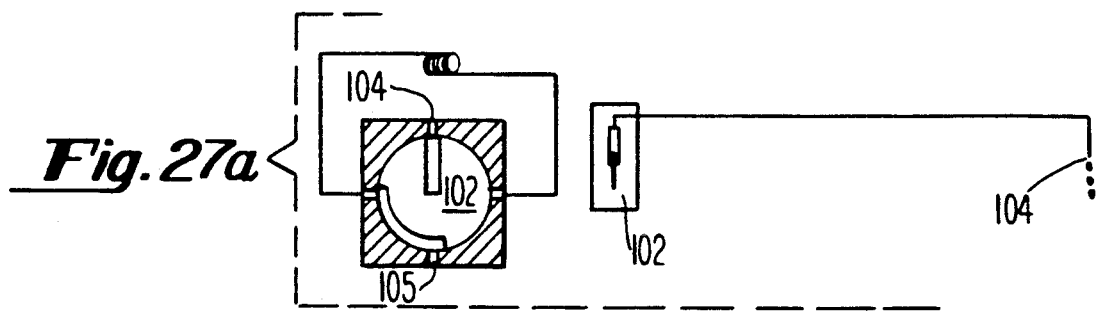
FIGS. 27a-27d show possible plug orientations for a flow system corresponding to the system depicted in FIG. 26, comprising a radial 4-port valve assembly in place of the axial 4-port valve assembly.
Figure 27B:
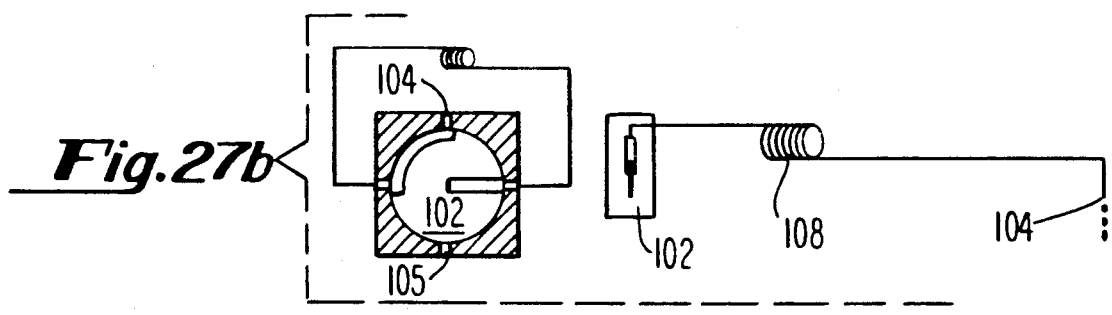
Figure 27C:
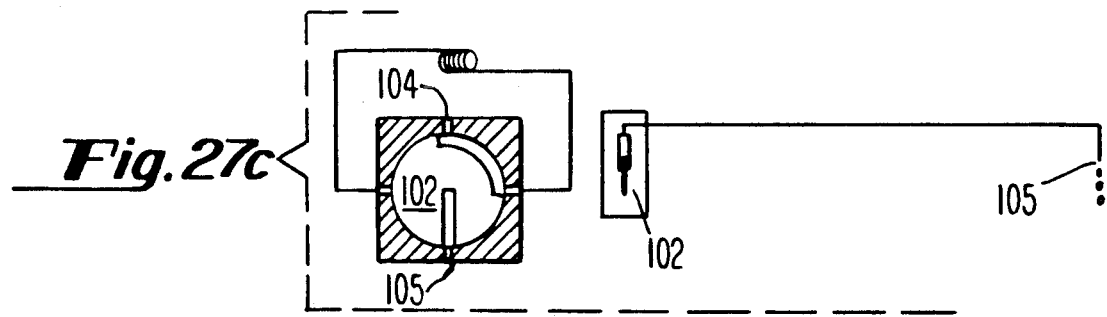
Figure 27D:
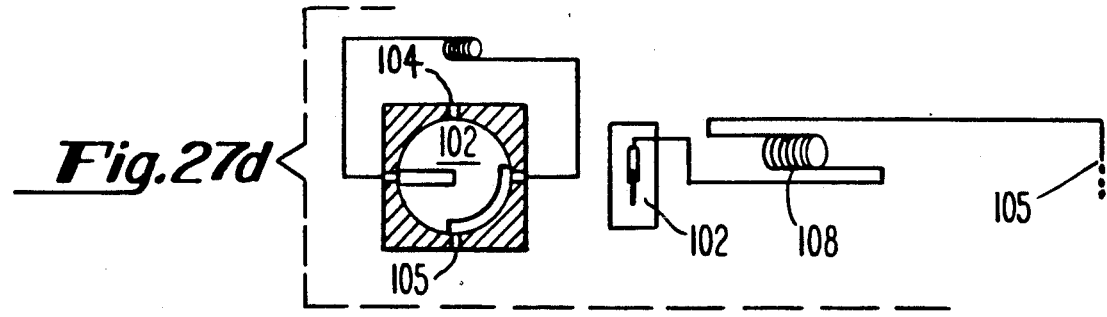
Figure 28:
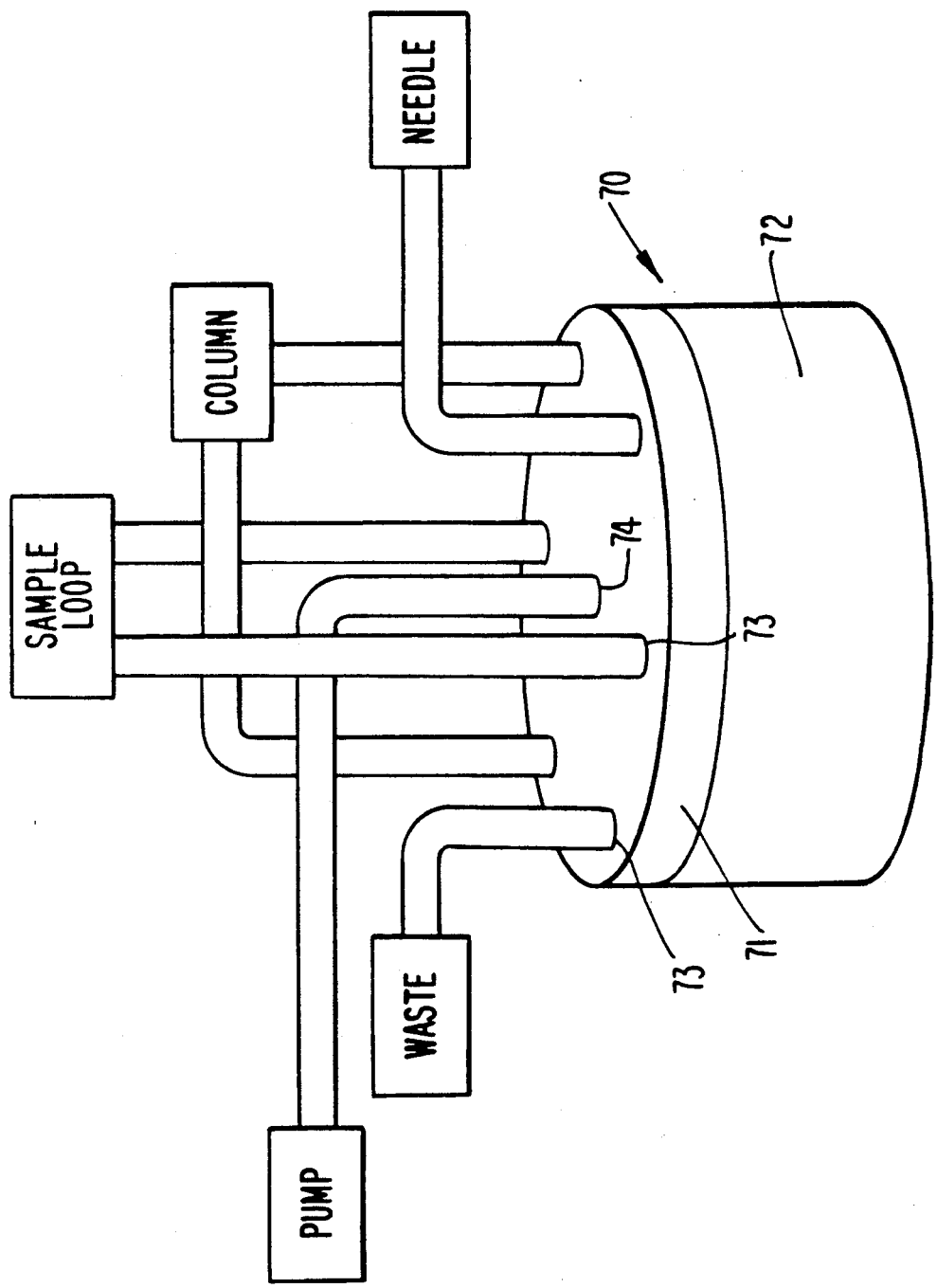
FIG. 28 depicts a flow system according to the present invention, comprising an axial 6-port valve assembly.

FIGS. 27a–27d demonstrate a 4-port flow configuration employing the present invention. The four diagrams display the flow patterns available at each of the four unique positions of the valve. FIGS. 27a and 27c demonstrate configurations suitable for minimum volume dispensing to needle (104) and needle (105), respectively. FIGS. 27b and 27d demonstrate configurations suitable for aspiration.

The four flow paths of FIGS. 27a–27d provide significantly enhanced performance of the dispenser/aspirator functions of the pump (102). First, the paths provide for the two independent functions of low-volume dispensing and aspiration under optimum conditions. Second, these functions can be duplicated at two different needles (104 and 105) which may be remote from one another. Finally, since the two needles share the same sample loop, transfers of fluid between the needles is possible without contamination of the syringe. While each of these functions is individually available by means of valve arrangements according to the prior art, no single prior art valve configuration provides all four flow patterns in a 4-port valve.

EXAMPLE 2

An analysis of desired flow paths for a solid phase extraction (SPE) device has been performed in which the device functions not only as an SPE device, but also as a dispenser. Six desired flow paths are shown in FIGS. 29a–29f.

FIG. 29a demonstrates a direct connection between the pump (102) and the needle (104). This path would be used in dispensing small volumes of reagent accurately, or in washing the needle.

FIG. 29b shows a path which connects the pump (102) to the needle (104) through a sample loop (108). This path is used for aspiration of samples from vials into the sample loop for later transfer to either the SPE cartridge or another vial.

The path shown in FIG. 29c allows flow from the pump (102) through the sample loop (108), through an SPE column (110), and then to the needle (104). This path is used for applying a sample stored in the sample loop onto the SPE column.

The path shown in FIG. 29d bypasses the sample loop (108) and flows directly from the pump (102) through the column (110) to the needle (104). This path solves the problem of the long lead volume between the pump and the column. Column conditioning, washing, and elution of the analyte would be done by this path. Also, this path eliminates the need to load the sample only after the column is conditioned, since sample may be stored in the sample loop while other functions are occurring.

FIG. 29e shows a path which flows from the pump (102) to waste (106). This path allows for changing solvents in the syringe without having to remove vials from under the needle (104). Note that the position referred to as "waste" could also be a needle on a remote dispenser.

The path shown in FIG. 29f flows from the pump (102) in the reverse direction through the column (110), through the sample loop (108), and then to waste (106). This path allows backflushing of the column into the sample loop. Backflushing allows the sample to be removed from the column with a minimum amount of solvent. Setting the path to the sample loop allows the fraction to be retained either for delivery to a vial or to a second SPE column for multiple column extraction methods. This permits multi-column extractions without the need for an intermediate vial.

In analyzing the flow patterns in FIGS. 29a-29f, a pump should always be connected to the common port to achieve the six illustrated configurations. Also, it is desirable to prevent uncontrolled flow to the components by closing all flow paths which are not connected to the pump. These requirements appear to suggest that the valve must have properties of distribution valve having at least 6 peripheral ports. However, further examination indicates that the flow patterns must be more than just point-to-point connections, since four items (SPE column (110), sample loop (108). needle (104), and waste (106)) must be connected in six different combinations. Such connectivity is one property of a selection valve.

Thus, the valve assembly shown in FIGS. 29a-29f is a hybrid of prior art switching and distribution valves. This valve has six unique flow orientations. Each orientation consists of the distribution channel connecting the common axial port to one peripheral port. Two pairs of peripheral ports are connected internally by the remaining channels and the final peripheral port is sealed against flow.

A flow system such as shown in FIGS. 29a-29f offers a number of advantages. For example, the system achieves bidirectional positive hydraulic displacement flow through the column bed. The column (110) may be backflushed to elute sample in the minimum volume, such as shown in FIGS. 29c, 29d, and 29f.

Another advantage is the provision of a direct path from pump (102) to waste (106) for exchanging solvents within the syringe without disturbing the rest of the flow system. This path is shown in FIG. 29e.

A further advantage is the provision of a low volume elution path to needle (104), such as shown in FIG. 29d, wherein both flow rate and elution volume are better controlled.

Another advantage is that the flow system provides intermediate sample loop (108) storage of eluent. This is desireable for multi-column cleanup. The path shown in FIG. 29f does not require an intermediate vial, thus reducing the number of vials required.

Also, sample loop loading, shown in FIG. 29b, need not follow column conditioning, which is shown in FIG. 29d. That is, a column (110) may be conditioned while sample is already in the loop (108).

The flow system additionally has a low volume dispensing path, shown in FIG. 29a, which reduces the amount of rinsing required. This is desirable for expensive reagents. The high volume aspiration path shown in FIG. 29b protects the syringe.

EXAMPLE 3

FIGS. 29a-29f demonstrate the six flow paths available to a 6-port valve assembly according to the present invention. If the sample loop (108) and the needle (104) in this figure are respectively replaced by a second column and a detector, the resulting flow system is suitable to serve as an HPLC flow system having automated purge and column switching path selection. The choice of flow paths provides a user the choice of configuring the system for constant use or for switching between flow paths without disconnecting components.

At least one of the flow paths shown in FIGS. 29a-29f also connects directly to waste (106). This is important, since HPLC pumps generally must be primed to flow paths with very low back pressure. The introduction of bubbles into the pump head may require re-priming during normal operation, which would normally require manual disconnection of one of the components or the addition of valves to allow this low back pressure path.

EXAMPLE 4

FIGS. 31a-31d and 32a-32d demonstrate an 8-port valve according to the present invention. Here, three terminal components—A, E, and F—as well as three flow-through components—B, C, and D—are configured into the flow system. The resulting flow paths demonstrate the variety of combinations in which the components may be ordered in the flow system.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A valve assembly for the regulation of fluid flow, comprising:
   a housing comprising a common port and n peripheral ports, wherein n is an even integer at least equal to 4; and
   a valve plug positioned to rotate within the housing, comprising:
   a distribution channel capable of fluid communication with the common port and each of the peripheral ports upon rotation of the valve plug; and
   (n/2)−1 switching channels, each switching channel capable of simultaneous fluid communication with at least two of the peripheral ports upon rotation of the valve plug.

2. The valve assembly of claim 1 wherein n is at least 4 and no greater than 8.

3. The valve assembly of claim 1 wherein n is 6.

4. The valve assembly of claim 1 wherein the housing comprises an outer face.

5. The valve assembly of claim 4 wherein the outer face comprises at least one peripheral port.

6. The valve assembly of claim 4 wherein the outer face comprises the common port.

7. The valve assembly of claim 1 wherein the housing comprises a sleeve.

8. The valve assembly of claim 7 wherein the sleeve comprises at least one peripheral port.

9. The valve assembly of claim 7 wherein the sleeve comprises the common port.

10. The valve assembly of claim 1 wherein the housing comprises a material selected from the group consisting of stainless steel and polymers which are inert to the fluid.

11. The valve assembly of claim 1 wherein the housing comprises a polymer selected from the group consisting of poly(tetrafluoroethylene) and poly(chlorotrifluoroethylene).

12. The valve assembly of claim 1 wherein the plug comprises an end face.

13. The valve assembly of claim 12 wherein the end face comprises the distribution channel.

14. The valve assembly of claim 12 wherein the end face comprises at least one switching channel.

15. The valve assembly of claim 1 wherein the plug comprises a body having a lateral face.

16. The valve assembly of claim 15 wherein the lateral face comprises the distribution channel.

17. The valve assembly of claim 15 wherein the lateral face comprises at least one switching channel.

18. The valve assembly of claim 1 wherein the plug comprises a polymer which is inert to the fluid.

19. The valve assembly of claim 1 wherein the plug comprises a polymer selected from the group consisting of poly(tetrafluoroethylene) and poly(chlorotrifluoroethylene).

20. The valve assembly of claim 1 wherein the plug is circular.

21. The valve assembly of claim 1 wherein the plug is conical.

22. The vale assembly of claim 1 wherein the distribution channel and switching channels are semi-circular grooves.

23. A system for the regulation of fluid flow, comprising:
at least one terminal component;
a vale assembly in fluid communication with the terminal component, comprising:
a housing comprising a common port and n peripheral ports, wherein n is an even integer at least equal to 4; and
a valve plug positioned to rotate within the housing, comprising:
a distribution channel capable of fluid communication with the common port and each of the peripheral ports upon rotation of the valve plug, and
$(n/2)-1$ switching channels, each switching channel capable of simultaneous fluid communication with at least two of the peripheral ports upon rotation of the valve plug; and
at least one flow-through component in fluid communication with the valve assembly.

24. The system of claim 23 wherein the terminal component is selected from the group consisting of fluid pumps, needles, tubing, sorbent columns, solid phase support reins, sample loops, and waste drains.

25. The system of claim 23 wherein the terminal component is selected from the group consisting of fluid pumps, needles, and waste drains.

26. The system of claim 23 wherein the flow-through component is selected from the group consisting of tubing, sorbent columns, solid phase support resins, and sample loops.

* * * * *